(12) United States Patent
Zavrel et al.

(10) Patent No.: US 9,637,434 B2
(45) Date of Patent: May 2, 2017

(54) METHOD FOR OBTAINING ETHANOL DURING FERMENTATION

(75) Inventors: Michael Zavrel, München (DE); Michael Kraus, Punchheim (DE); Sandra Hofmann, Röttingen (DE); Ulrich Kettling, München (DE); Andre Koltermann, Icking (DE); Christian Ott, Ampfing (DE); Zdravko Dragovic, München (DE)

(73) Assignee: SUD-CHEMIE IP GMBH & CO. KG, München (DE)

(*) Notice: Subject to any disclaimer, the term of this patent is extended or adjusted under 35 U.S.C. 154(b) by 78 days.

(21) Appl. No.: 13/514,510

(22) PCT Filed: Dec. 8, 2010

(86) PCT No.: PCT/EP2010/069161
§ 371 (c)(1),
(2), (4) Date: Jan. 2, 2013

(87) PCT Pub. No.: WO2011/070061
PCT Pub. Date: Jun. 16, 2011

(65) Prior Publication Data
US 2013/0095543 A1   Apr. 18, 2013

(30) Foreign Application Priority Data
Dec. 8, 2009  (EP) ..................................... 09178390

(51) Int. Cl.
| | | |
|---|---|---|
| C12P 7/06 | (2006.01) | |
| C07C 29/84 | (2006.01) | |
| C07C 29/76 | (2006.01) | |
| C12P 7/10 | (2006.01) | |

(52) U.S. Cl.
CPC .............. *C07C 29/84* (2013.01); *C07C 29/76* (2013.01); *C12P 7/06* (2013.01); *C12P 7/10* (2013.01); *Y02E 50/16* (2013.01); *Y02E 50/17* (2013.01)

(58) Field of Classification Search
None
See application file for complete search history.

(56) References Cited

U.S. PATENT DOCUMENTS

| | | | | |
|---|---|---|---|---|
| 3,702,886 A | | 11/1972 | Argauer et al. | |
| 3,936,353 A | * | 2/1976 | Chen .......................... | C07C 1/20 435/163 |
| 4,359,592 A | * | 11/1982 | Chao et al. .................... | 568/916 |
| 4,420,561 A | * | 12/1983 | Chen et al. .................... | 435/161 |
| 4,515,892 A | | 5/1985 | Chen et al. | |
| 4,665,027 A | | 5/1987 | Dale et al. | |

FOREIGN PATENT DOCUMENTS

| | | |
|---|---|---|
| CN | 101265159 | 9/2008 |
| EP | 0216221 B1 * | 7/1994 |
| EP | 2 333 092 B1 | 12/2009 |

OTHER PUBLICATIONS

Rosenberg et al. (Lawrence Berkeley National Laboratory, p. 1-40, 1980).*
Hashi M. et al, Energy and Fuels, vol. 24, No. 9, 2010, pp. 4628-4637.
Database Energy Citations Database Feb. 1983, Walsh P. K. et al, Biotechnology and Bioengineering Symposium, No. 13, 5th Symposium on Biotechnology for Fuels and Chemicals; USA.
Vane L.M.; Biofuels, Bioproducts and Bioengineering, vol. 2, No. 6, 2008, pp. 553-588.
Dominguez J. M. et al, Biotechnology and Bioengineering, vol. 67, No. 3, 2000, pp. 336-343.
Database WPI Week 200830 Thomson Scientific, London, GB, & CN 101 024 846 A (Univ. Fudan), 2007.
Database EPODOC, 2008, & CN 101 265 159 A (Shanghai Lead Biotechnology Co.), 2008.
Database WPI, Week 200873, AN 2008-M35536; & CN 101 225 017 A (Univ. Fudan), 2008.
Yang, R.T.: "Gas separation by adsorption processes", 1997, Imperial College Press, London, pp. 1-8, 23-26.
Carton et al., Bioresource Technology, vol. 66, No. 1, 1998, pp. 75-78.
Caputo et al., Microporous and Mesoporous Materials, vol. 105, No. 3, 2007, pp. 260-267.
Oumi Y. et al., "Binary mixture adsorption of water and ethanol on silicalite", Elsevier Science B.V., 2002, pp. 1595-1601.
Aguayo A.T. et al., "Study of operating variables in the transformation of aqueous ethanol into hydrocarbons on an HZSM-5 zeolite", Society of Chemical Industry, 2002, J. Chem. Technol. Biotechnol.
Costa E. et al., "Ethanol to Gasoline Process: Effect of Variables, Mechanism and Kinetics", American Chemical Society, 1985, pp. 239-244.
International Search Report for PCT/EP2010/069161, dated May 13, 2011.
European Search Report for EP 09178390, dated May 10, 2010.
Minquan Zhang et al. "In situ separation of ethanol fermentation by CO2 striping and activated adsorption processes II. Free cell continuous fermentation" Chemical Reaction Engineering and Technology, vol. 6, Issue 1, Mar. 1990.
English translation of Office Action issued in CN 20108006321.4, on Sep. 24, 2013.
U.S. Appl. No. 13/001,860, filed Dec. 29, 2010, Decomposition of Materials Containing Carbohydrates Using Inorganic Catalysts.
U.S. Appl. No. 13/121,827, filed May 26, 2011, Recovery and Purification Process for Organic Molecules.
U.S. Appl. No. 13/143,019, filed Sep. 8, 2011, Process for Cell-Free Production of Chemicals.
U.S. Appl. No. 13/322,395, filed Jan. 24, 2012, Liquefied Biomass.
U.S. Appl. No. 13/517,344, filed Jan. 15, 2013 Thermostable (Continued)

*Primary Examiner* — Chris R Tate
*Assistant Examiner* — Douglas F White
(74) *Attorney, Agent, or Firm* — Gianna Julian-Arnold; Saul Ewing LLP

(57) ABSTRACT

The invention relates to a method for obtaining ethanol from a carbohydrate-containing raw substrate wherein the ethanol that is produced is separated during fermentation using a carrier gas. The invention further relates to the adsorption of the ethanol from the gas phase to an adsorber, the desorption of the ethanol during a subsequent process step, and to the further concentration of the ethanol.

18 Claims, 8 Drawing Sheets

(56) References Cited

OTHER PUBLICATIONS

Xylanase for the Selective Hydrolysis of Pentose-Containing Polysaccharides.

* cited by examiner

METHOD FOR OBTAINING ETHANOL DURING FERMENTATION

RELATED APPLICATIONS

This application is a 35 U.S.C. §371 national stage filing of International Application No. PCT/EP2010/069161, filed Dec. 8, 2010, which is related and claims priority to EP Application Serial No.: 09 178 390.2, filed Dec. 8, 2009. The entire contents of these applications are explicitly incorporated herein by reference.

FIELD OF THE INVENTION

The invention relates to a method for preparing ethanol by fermentation.

BACKGROUND OF THE INVENTION

During fermentation of raw substrates containing carbohydrates, yeasts or bacteria are capable of converting the sugar monomers consisting of five ("C5 sugars", pentoses) and/or six carbon atoms ("C6 sugars", hexoses) into ethanol (Huber et al., Chem. Rev. 2006, Vol. 106, pp. 4044 to 4098). Ethanol is called "bio-ethanol" when it is prepared from biogenic raw materials. Bio-ethanol is suitable as a bio-fuel, as an admixture to petrol for spark-ignition engines or for further chemical processing. In the past, it has primarily been recovered from sugar and grain containing starch, but so far not from ligno-cellulose biological (LCB) matter in amounts worth speaking of (Huber et al., Chem. Rev. 2006, Vol. 106, pp. 4044 to 4098; Kamm and Kamm, Chem. Ing. Tech., 2007, Vol. 79, pp. 592 to 603).

Separation of the ethanol from the fermentation solution is necessary for preparing ethanol by fermentation. These techniques include pervaporation, extraction, adsorption, reverse osmosis and gas stripping (Windsperger et al., Verfahrenstechnik 1989, Vol. 23, pp. 16 to 21; Qureshi et al., Bioprocess Biosyt. Eng. 2005, Vol. 27, pp. 215 to 222). In particular, the ethanol may be converted to the gas phase. Gas stripping is a selective removal of volatile substances from the fermentation solution (Ezeji et al., J. Ind. Microbiol. Biotechnol. 2007, Vol. 34, 771 to 777).

After conversion to the gas phase, the ethanol needs to be separated from the ethanol-gas mixture. In particular, the ethanol must be separated from the ethanol-carrier gas mixture after stripping. Different techniques are available for this purpose, such as condensation or selective adsorption of the ethanol to an adsorber. CA 1 195 258, for example, describes a process where the fermentation solution is subjected to gas stripping after fermentation has been completed and the ethanol-carrier gas mixture is then adsorbed to a molecular lattice under conditions avoiding the capillary condensation of water. However, this process does not allow controlling the ethanol concentration during fermentation.

However, such control of the ethanol concentration in the fermentation solution is important for preparing bio-ethanol at an industrial scale. One problem in the production of bio-ethanol is the increasingly inhibiting effect and the toxic influence of the ethanol formed on the micro-organisms during fermentation. As a result of the inhibiting effect and the toxic influence of products formed during fermentation, various techniques have been developed to separate these in situ during fermentation.

For example, Walsh et al. (Biotechnology and Bioengineering Symp., No. 13, 1983, pp. 629 to 647) describe a method where C6 sugar is fermented to obtain ethanol and the ethanol is separated from the fermenter in situ by gas stripping and adsorbed to activated carbon. This method permits adjusting the ethanol concentration during fermentation in the range around 6% (w/v). Given the low selectivity of activated carbon for ethanol, however, activated carbon is not suitable for an efficient process.

However, such a control at 6% (w/v) is not sufficient for preparing ethanol from ligno-cellulose bio-matter which requires the fermentation of C5 sugars. For example, Dominguez et al. (Biotech. Bioeng., 2000, Vol. 67, pp. 336-343) have been able to show that the reaction of C5 sugars to form ethanol with the yeast *Pichia stipitis* is inhibited at only 2% (w/v) of ethanol. Therefore, Dominguez et al. have developed a process where the ethanol concentration may be kept below 2% (w/v) during the fermentation of xylose, with ethanol being condensed on an ice-cooled condenser after stripping in situ in an especially designed fermenter with a side arm.

SUMMARY OF THE INVENTION

Against this background, it was the object of the invention to provide an efficient method for preparing ethanol by fermentation which permits a high ethanol yield when using mixtures of C5 and C6 sugars as obtained from ligno-cellulose bio-matter, for example.

Surprisingly, it has been found that a combination of in-situ stripping and a zeolite adsorber not only permits keeping the ethanol concentration in the fermentation solution below 5% (w/v) during the entire duration of the fermentation, but that the use of a zeolite adsorber allows a particularly energy-saving process management. Therefore, the invention provides a method for preparing ethanol, comprising:

a) the fermentative reaction of C5 and/or C6 sugars to obtain ethanol in a fermentation solution;
b) in-situ removal of the ethanol by conversion to the gas phase;
c) passing the resulting ethanol-carrier gas mixture obtained by gas stripping through a zeolite adsorber where ethanol is adsorbed from the gas mixture to an adsorber; and
d) desorption of the adsorbed ethanol from the adsorber.

FIGURES

DETAILED DESCRIPTION OR THE INVENTION

Fermentation of C5 and C6 Sugars

Figure 1:
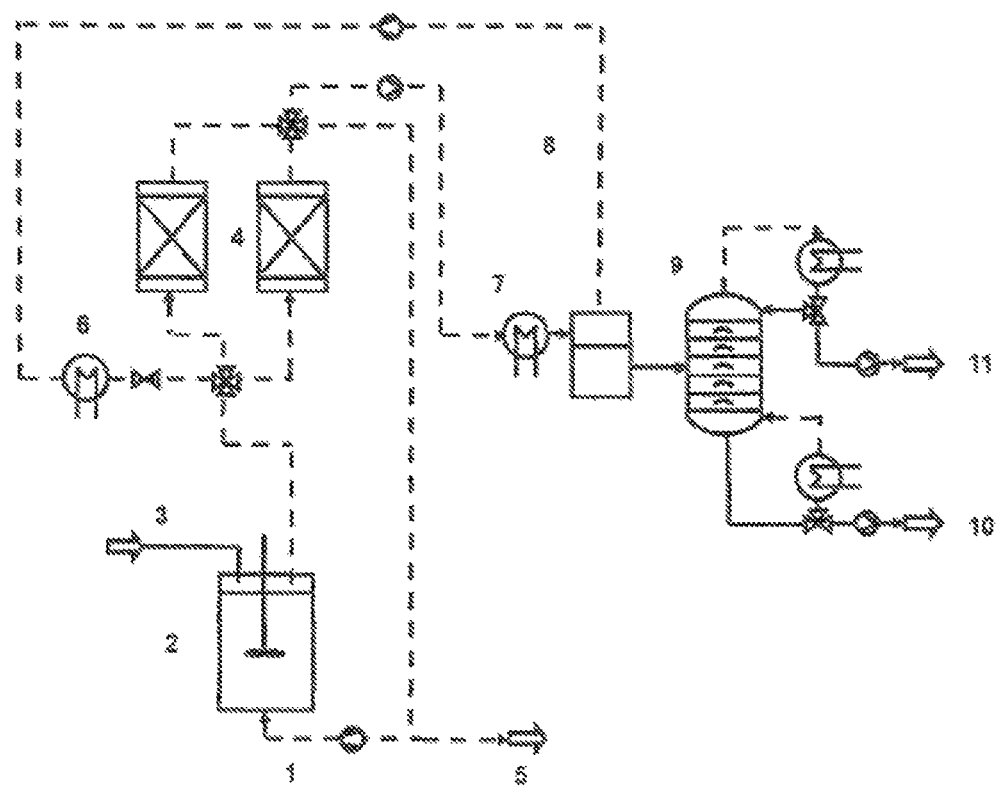
FIGS. 1a and 1b show exemplary embodiments of the method of the invention with gas stripping in the fermenter (1a) and an external gas stripping column (1b).

A solution with C5 and C6 sugars is provided for fermentation. It is preferred that the solution initially contain less than 200 g/L of sugar of which less than 100 g/L, preferably less than 80 g/L, and especially preferably less than 70 g/L should be C6 sugar and less than 100 g/L, preferably less than 35 g/L and especially preferably less than 30 g/L should be C5 sugar. In a particularly preferred embodiment, the solution contains less than 120 g/L of sugar, 90 or more % of the sugars being C6 sugar. In a further particularly preferred embodiment, the solution contains less than 120 g/L of sugar, 90 or more % of the sugars being C5 sugar. In a further particularly preferred embodiment, the solution contains less than 200 g/L of sugar, preferably less than 120 g/L of sugar, 20 to 40% of the sugars being C5 sugar and, accordingly, 60 to 80% being C6 sugar. This solution is usually recovered from raw substrates containing carbohydrates. It may be required to digest these raw substrates by suitable pre-treatment processes and/or to hydrolyse the carbohydrates enzymatically or by acid catalysis to obtain sugar monomers. Optionally, the solution may be concentrated before fermentation.

The term "raw substrate containing carbohydrates" comprises pure substances containing carbohydrates, mixtures of different carbohydrates and complex mixtures of substrates containing carbohydrates. Material containing carbohydrates further comprises waste products from forestry and agriculture, the food-processing industry and communal waste. In particular, the materials containing carbohydrates include ligno-cellulose bio-matter (LCB) containing cellulose, hemi-cellulose and lignin. Agricultural LCB comprises grain straw and spelt (wheat, rye, barley, oats), maize straw and spindles, manure from stables, sugar cane pressed cake (bagasse), sugar beet pulp (sugar beet chips) and herbaceous materials and grasses such as *Sericea lespedeza*, switchgrass (*Panicum virgatum*), Napier grass (*Miscanthus*; China reed) and Sudan grass (*Sorghum sudananse, Sorghum drummondi*). LCB in the form of forestry waste comprises barks, wood chips and chippings inter alia. LCB in the form of raw substrates from the food industry comprises, among other things, fruit pulp, agave residues, coffee grinds and waste from oil mills such as rapeseed pressed cake and sewage from mills LCB in the form of raw substrates from the wood pulp and paper industry includes paper-making stock and waste water from paper mills. LCB in the form of raw substrates from communal waste includes, but is not limited to, waste paper, vegetable and fruit leftovers. The fermentation solution is preferably obtained from LCB by hydrolysis. Additional additives such as pH standardisers may be added to the solution.

The C5 and/or C6 sugars, preferably C5 sugar, optionally together with C6 sugar, released upon hydrolysis are converted to ethanol by fermentation. According to the preferred embodiment of the invention, yeasts and bacteria are used. Especially preferred are yeasts metabolising C5 and C6 sugars and particularly those the fermentation activity of which is inhibited at ethanol concentrations above 5% (% w/v).

According to the process of the invention, the temperature of the fermenter is between 10 and 100° C., preferably between 10 and 50° C., especially preferably between 20 and 50° C., most preferably between 20 and 50° C. It is preferred to use mesophilic yeasts such as *Pichia stipitis*, *Pichia segobiensis*, *Candida shehatae*, *Candida tropicalis*, *Candida boidinii*, *Candida tenuis*, *Pachysolen tannophilus*, *Hansenula polymorpha*, *Candida famata*, *Candida parapsilosis*, *Candida rugosa*, *Candica sonorensis*, *Issatchenkia terricola*, *Kloeckera apis*, *Pichia barkeri*, *Pichia cactophila*, *Pichia deserticola*, *Pichia norvegensis*, *Pichia membranefaciens*, *Pichia mexicana* and *Torulaspora delbrueckii*.

In an alternative embodiment, thermophilic micro-organisms are used. Examples of thermophilic yeasts are *Candida bovina*, *Candida picachoensis*, *Candida emberorum*, *Candida pintolopesii*, *Candida thermophila*, *Kluyveromyces marxianus*, *Kluyveromyces fragilis*, *Kazachstania telluris*, *Issatchenkia orientalis* and *Lachancea thermotolerans*. Thermophylic bacteria include, among others, *Clostridium thermocellum*, *Clostridium thermohydrosulphuricum*, *Clostridium thermosaccharolyticum*, *Thermoanaerobium brockii*, *Thermobacteroides acetoethylicus*, *Thermoanaerobacter ethanolicus*, *Clostridium thermoaceticum*, *Clostridium thermoautotrophicum*, *Acetogenium kivui*, *Desulfotomaculum nigrificans* and *Desulvovibrio thermophilus*, *Thermoanaerobacter tengcongensis*, *Bacillus stearothermophilus* and *Thermoanaerobacter mathranii*. The use of the following mesophilic yeasts is especially preferred: *Saccharomyces cerevisiae*, *Pichia stipitis*, *Pachysolen tannophilus*, *Candida shehatae*.

Fermentation is preferably conducted in a batch mode (discontinuous), in the fed-batch mode or in a continuous mode. Most preferably, fermentation is conducted in the batch mode.

In-situ Stripping

According to the present invention, the volatile components, especially the product ethanol, are converted to the gas phase especially by stripping with an inert carrier gas.

The in-situ removal of the ethanol means the removal of the ethanol, for example by gas stripping, in parallel to its fermentative preparation. This may either be carried out continuously or discontinuously. In the continuous mode, sugar is simultaneously reacted to form ethanol and at least one portion of this ethanol removed, for example by gas stripping. In the discontinuous mode, at least one portion of the sugar is converted to ethanol by fermentation and then at least one portion of the ethanol is removed, for example by gas stripping. After that, at least one portion of the sugar is converted to ethanol, etc. In another discontinuous mode, sugar is continuously converted to ethanol, but the ethanol is removed only periodically, for example by gas stripping.

The in-situ removal of the ethanol may be conducted by gas stripping, by pervaporation or by comparable methods for converting the ethanol to the gas phase. Conversion to the gas phase may take place either in the fermentation vessel or in a separate apparatus.

A carrier gas is preferably used for conversion by means of gas stripping. Suitable carrier gases are gases such as carbon dioxide, helium, hydrogen, nitrogen or air and mixtures thereof. Carbon dioxide and mixtures of carbon dioxide and air are especially preferred; where necessary, micro-aerobic conditions may be adjusted. One advantage of this embodiment of the method of the invention is that carbon dioxide formed during fermentation may be used directly as the carrier gas.

According to the method of the invention, fermentation is carried out in a stirred tank or a loop-type bubble column or an air-lift reactor. Gas exchange is also possible via an external gas stripping column connected to the fermenter. This column is continuously fed with the fermentation solution, and its discharge is returned to the fermenter. It is especially preferred to operate such an external gas stripping column in a counter-current and/or in combination with filler materials for an increased exchange of materials, such as Raschig rings.

The specific gassing rate is preferably between 0.1 and 10 vvm, especially preferably between 0.5 and 5 vvm.

Stripping is preferably conducted at a pressure between 0.1 and 2 bar, especially preferably between 0.5 and 1.1 bar. Stripping at a sub-pressure is especially preferred.

So as to achieve efficient gas stripping in the fermenter, the gas bubbles are preferably dispersed. This may be done with a stirrer arranged in such a manner that fine bubbles of the carrier gas are formed.

In a preferred embodiment, the in situ removal of ethanol from the fermentation solution is carried out at the temperature of fermentation. Thus no additional thermal energy is needed for heating the fermentation solution.

It is a further advantage of the method of the invention that the evaporation enthalpy resulting from the conversion of the volatile substances from the liquid to the gas phase contributes to cooling the fermenter, thus reducing the energy required for keeping the temperature of the fermenter at a constant level.

Adsorption

According to the method of the invention, the gas stream leaving the fermenter is guided through one or more columns filled with one or more kinds of adsorbents. At least one of the columns contains a zeolite as the adsorber. Other suitable adsorbents are silica, bentonites, silicalites, clays, hydrotalcites, aluminium silicates, oxide powders, mica, glasses, aluminates, clinoptolites, gismondines, quartzes, activated carbons, bone char, montmorillonites, polystyrenes, polyurethanes, polyacryl amides, polymethacrylates or polyvinyl pyridines. In a particularly preferred embodiment, only zeolites are used as adsorbents.

Zeolites are preferred; zeolites of the beta or MFI type are especially preferred. The zeolite preferably has an $SiO_2/Al_2O_3$ ratio from 200 to 1,000 and, especially preferably, the $SiO_2/Al_2O_3$ ratio is 400 to 800. The synthetic zeolites of U.S. Pat. No. 7,244,409 are especially preferred.

The weight ratio of the adsorbent to the adsorbed ethanol is preferably between 1 and 1,000, especially preferably between 5 and 20.

When ethanol is adsorbed to the adsorbent (the adsorbents), the adsorption enthalpy is released which causes the packing to heat. Owing to the low heat conductivity of the possible adsorbent materials described and the cavity volume within the bed, this heat cannot be discharged effectively via the wall of the column, especially in the case of large column diameters. Therefore, heating coils within the columns permitting the discharge of the released adsorption enthalpy are used in addition in a preferred embodiment of the present invention. It is one advantage of this embodiment that energy for the subsequent energy-consuming process step may be recovered.

Suitable heating coils are tubes through which a fluid flows and which thus permit both the charge and discharge of thermal energy. Alternatively, heating coils that may be heated electrically may be used.

According to the method of the invention, the temperature may be influenced and kept at a constant level through the heating coils within the column. This permits influencing the selectivity of the adsorbent. In a preferred embodiment of the process, selectivity is controlled not only by the temperature, but also by the pressure within the column.

The temperature during the adsorption of the ethanol is preferably between 10 and 100° C., especially preferably between 20 and 50° C. The pressure is preferably between 0.5 and 10 bar, especially preferably between 1 and 2 bar.

It is especially preferred to conduct the adsorption at a temperature that does not exceed the temperature of the ethanol-carrier gas mixture upon discharge from the fermentation solution. In a particularly preferred embodiment, neither the ethanol-gas mixture nor the adsorber is heated before adsorption. In addition, it is especially preferred to conduct the adsorption at excess pressure.

In a preferred embodiment, at least one C5 sugar is present in the fermentation solution in this process. This also includes fermentation solutions comprising mixtures of at least one C5 sugar and at least C6 sugar. It is especially preferred to react the at least one C5 sugar present in the fermentation solution to form ethanol.

The amount of the adsorber material used is preferably adjusted to the amount of the ethanol formed by fermentation. The amount of the ethanol adsorbed at the end of fermentation is preferably at least 20%, more preferably at least 50% and especially preferably at least 90% of the maximum ethanol uptake of the adsorber. Both the amount of ethanol resulting from fermentation and the maximum ethanol amount to be taken up by the adsorber can be determined before fermentation. Gas stripping and adsorption take place exactly as described in example 2 for determining both parameters, i.e. a solution with a known ethanol concentration is fed in and then stripped continuously. During this time, the ethanol concentration in the feed is measured every hour. When this stops changing (after 24 hours at the latest), the capacity of the adsorber material is exhausted. The experiment is then terminated and the volume of the feed and the concentration of the ethanol contained therein determined so that the weights of ethanol and water can be calculated. The differences between the initial weights and the weights after the end of the experiment result in the weights of ethanol and water adsorbed (mass balance). On the basis of these results, the concentration of the ethanol adsorbed and the capacity of the adsorber material may be determined. The maximum amount of ethanol formed during fermentation can be estimated with the aid of the theoretical yield coefficients. The theoretical yield coefficients are 0.51 g of ethanol per 1 g of glucose and, respectively, 0.46 g of ethanol per 1 g of xylose (Lee et al., J. Microbiol. Biotechn., 2001, vol. 11 (3), pp. 384 to 388). The ethanol yields achieved in practical applications are between 70 and 100%, typically 90 to 95% of the theoretical yields. The required adsorber amount is calculated on the basis of the amount of ethanol expected plus an extra of typically 10 to 20%.

The adsorber material may be contained in one or more columns. Preferably, several, especially preferably 2 to 6, columns are used. These columns may be operated in series or in parallel.

The advantages of parallel operation are, on the one hand, that quasi-continuous operation is permitted in that two or more columns alternate between adsorption and desorption and, on the other hand, that the thermal energy released during adsorption may be transferred to the desorption step in a different column, i.e. that adsorption and desorption may be conducted simultaneously in different columns. The columns are preferably provided in a rotary arrangement.

In a particularly preferred embodiment, 2 to 6 columns are operated in such a manner that the column(s) where desorption is conducted, is/are operated in parallel to the column(s) where desorption is conducted. If adsorption is conducted in more than one column, these columns may be operated in series. For example, adsorption may be conducted in columns 1 to 3 when 6 columns are used, e.g. in the rotary configuration, column 4 is heated for desorption, desorption is conducted in column 5 and column 6 is allowed to cool down. The adsorber column is changed when the amount of ethanol adsorbed contributes at least 90%, especially preferably at least 95% of the maximum ethanol uptake of the adsorbers in this column.

The method of the invention using several adsorption columns also makes it possible to operate two or more columns in series. Each of these columns is filled with different adsorbents which have different selectivities and/or capacities. In this alternative, the carrier gas preferably flows through the adsorbers in the order of ascending ethanol binding selectivities (based on water) during adsorption.

After leaving the adsorption column, the ethanol-depleted gas stream may be returned to the fermenter and is available for gas stripping once more.

Adsorption may be conducted in a fluid bed operation.

The ethanol concentration in the fermentation solution may be kept below 5% (w/v), preferably below 2% (w/v) throughout the entire duration of the fermentation with the combination of in-situ gas stripping and adsorption to a zeolite according to the invention. Fermentation is preferably conducted as long as ethanol is produced. Preferred fermentation times are 20 to 120 hours, especially preferably 30 to 80 hours.

Desorption

The method of the invention permits selective desorption of the ethanol from the adsorbent by raising the temperature and/or lowering the pressure within the column. In a preferred embodiment of the method, the thermal energy is applied to the adsorbent package via the column wall and, optionally, also via the heating coils inside the column. Temperatures between 25 and 300° C. and absolute pressures between 0 and 10 bar are preferred. Especially preferred are temperatures between 80 and 180° C. and absolute pressures at sub-pressure, preferably between 0.1 and 1 bar.

In accordance with the method of the invention, a carrier gas is used for discharging the desorbed ethanol from the column. It is preferred to use the same inert carrier gas also used for gas stripping. In one embodiment of the method of the invention, the temperature and the absolute pressure are adjusted within the column to the temperatures and absolute pressures described above. For this purpose, heat exchangers arranged upstream and/or throttles or compressors may be used.

Desorption may be conducted in a fluid bed operation.

Further Purification

A preferred embodiment of the process of the invention involves condensation of the desorbed ethanol gas. According to a preferred embodiment of the process, the gas stream is compressed and/or cooled by using one or more compressors and/or one or more heat exchangers and/or one or more cold traps. Counter-flow heat exchangers are particularly preferred. In a further preferred embodiment of the process of the invention, condensates with different ethanol concentrations are obtained by operating two or more heat exchangers and/or cold traps with different cooling temperatures in series. In addition, this permits the selective condensation of accompanying substances still present such as water or other volatile substances.

Condensation enthalpy is released during condensation. According to a preferred embodiment of the process of the invention, this thermal energy is transferred to earlier and/or possible subsequent process steps requiring energy. According to a particularly preferred embodiment of the process of the invention, these process steps requiring energy are the prior desorption of the ethanol and/or a possible subsequent rectification.

According to a further embodiment of the process of the invention, the condensed ethanol obtained is purified and concentrated further. A typical accompanying substance of the ethanol in the condensate is water. The removal of water and/or further accompanying substances may be carried out by rectification.

In a preferred embodiment of the process, the temperature during condensation of the ethanol is kept just below the boiling point of the resulting condensate so that the ethanol solution to be rectified is transferred to rectification near the boiling point, reducing the energy required for rectification. The energy required for rectification may be reduced further by means of vapour compression.

The water contained in the sump of the rectification column may be returned to the fermenter. At the top of the column, the azeotrope between ethanol and water is obtained. If it is desired to recover anhydrous ethanol, it is possible to use suitable separation processes afterwards, such as the removal of water by means of a molecular sieve or by using selective membrane processes. It is also possible to shift the position of the azeotrope by changing the pressure during rectification.

In accordance with an alternative embodiment of the process of the invention, the desorbed ethanol gas is passed through a further column before condensation so as to remove accompanying substances from the gas phase. In those cases, it is preferred to remove water by means of a molecular sieve. The application of vapour permeation is also possible in this alternative embodiment.

A further alternative embodiment of the process of the invention provides for passing the condensate obtained after desorption to a pervaporation step so that absolute ethanol may be achieved.

According to the process of the invention, the carrier gas stream recovered by condensation of the ethanol and other possible accompanying substances may be taken in a cycle so that no or just a little external addition of carrier gas is required for gas stripping in the fermenter.

Especially Preferred Embodiments

FIG. 1a shows a possible embodiment of the process of the invention. An inert carrier gas stream (1) is blown into the fermenter (2) for gas stripping. The LCB is fermented inside the fermenter to obtain ethanol, adding supplementary agents (3) such as pH standardizing agents.

The gas leaving the fermenter which contains ethanol and other volatile components is passed through an adsorption column (4) which adsorbs the ethanol selectively. So as to ensure quasi-continuous operation, two or more columns are operated in parallel and/or in series. Thermal exchange between the columns is achieved by using internal heating coils.

Part of the carrier gas stream is removed as a result of the carbon dioxide formed by fermentation.

The temperature and/or the pressure inside the columns (4) is changed to desorb the adsorbed ethanol. The carrier gas stream required for discharging the desorbed ethanol is adjusted accordingly by a heat exchanger (6) and/or throttles.

The gas leaving the column upon desorption is then condensed by means of compression and/or cooling (7). The carrier gas stream (8) thus regenerated is returned.

The condensate is passed to a rectification column (9) for further purification and condensation. Water (10) is obtained at the sump of the column and an azeotrope between ethanol and water (11) at the head of the column.

Figure 1B:
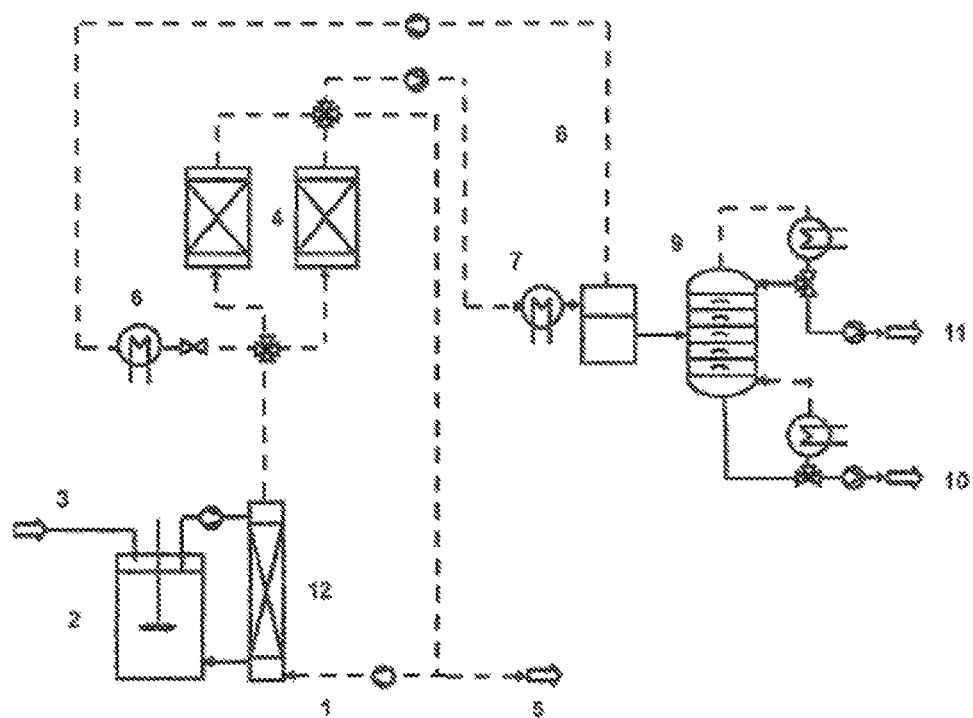

FIG. 1b shows another possible embodiment of the process of the invention, but, in this case, gas stripping is conducted in an external gas stripping column (12) connected to the fermenter. For this purpose, fermentation solution is passed to the external gas stripping column and the stripped solution is then returned to the fermenter. All other process steps are analogous to FIG. 1a.

Figure 4:
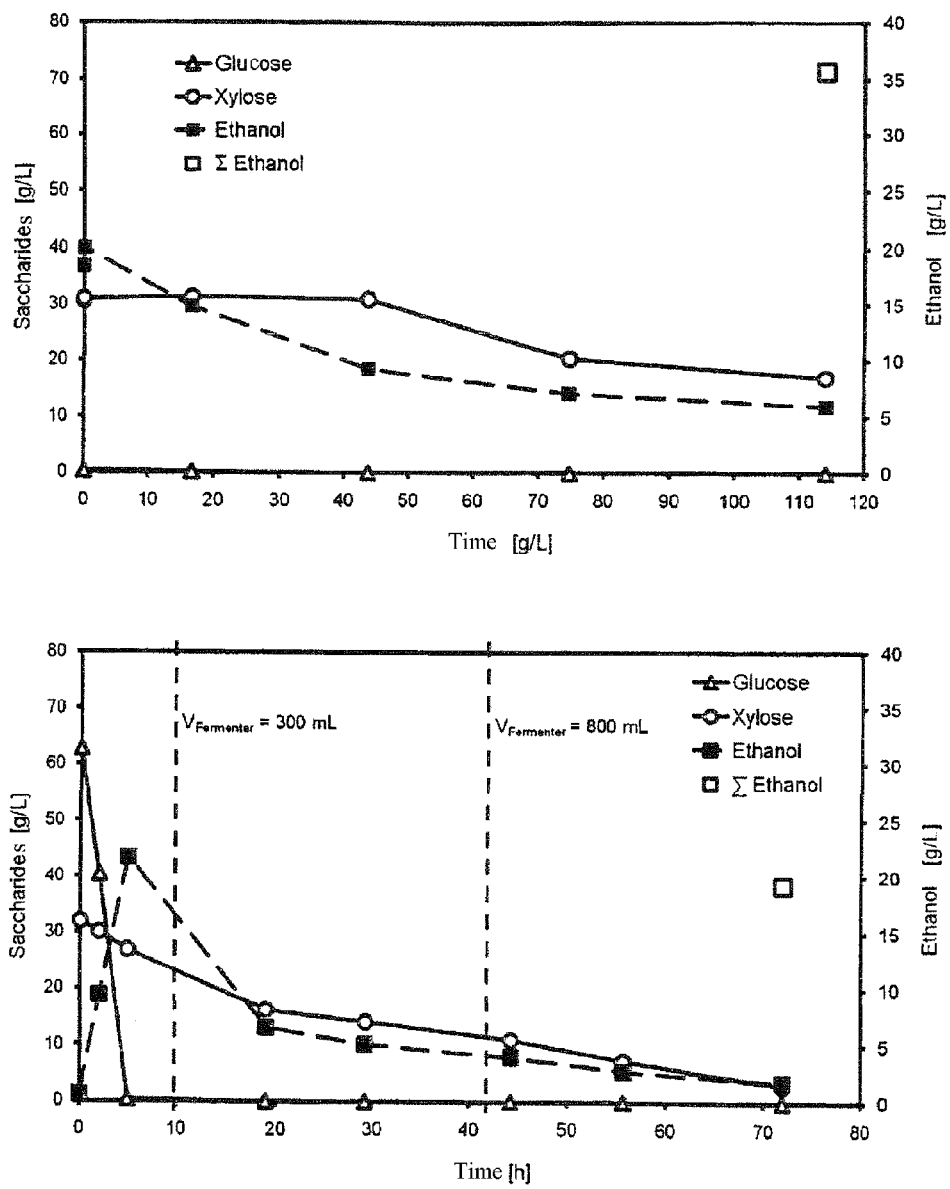
FIG. 4 shows the development of the glucose, xylose and ethanol concentration during fermentation according to example 1C.

FIG. 4 shows the rotary configuration where the three columns (A1-A3) are operated in series for adsorption of the stripping gas exiting the fermenter (F). The columns A4 to A6 are operated in parallel. Column A4 is heated (a), column A5 is desorbed (b), and column A6 is cooled (c). After the end of the cycle time, column A3 reaches the heating phase (a), A4 is desorbed (b) and A5 cooled (c). Columns A6, A1 and A2 are then operated in series for adsorption. After 6 cycle times, the same column is desorbed as at the outset so that one cycle is completed and a new one begins.

The following process is especially preferred in accordance with the invention:

A method for preparing ethanol, comprising
a) the fermentative reaction of C5 and/or C6 sugars to obtain ethanol in a fermentation solution;
b) in-situ removal of the ethanol by gas stripping with the aid of a carrier gas, the ethanol concentration in the fermentation solution being kept below 5% (w/v);
c) passing the resulting ethanol carrier gas mixture obtained by gas stripping through an adsorber where ethanol is adsorbed from the gas mixture to an adsorber in a first column;
d) desorption of the adsorbed ethanol from the adsorber in a second column;
e) heat resulting from the adsorption in the first column being used for heating the second column;
f) the carrier gas being returned to the fermentation solution after leaving the adsorber; and
g) concentration of the desorbed ethanol.

The following process is also especially preferred in accordance with the invention:

A method for preparing ethanol, comprising
a) the fermentative reaction of C6 sugars to obtain ethanol in a fermentation solution containing C5 and C6 sugars;
b) removal of the ethanol from the fermentation solution by gas stripping with the aid of a carrier gas;
c) the subsequent fermentative reaction of C5 sugars to obtain ethanol in the fermentation solution, the ethanol being removed in situ by gas stripping with the aid of a carrier gas and the ethanol concentration in the fermentation solution being kept below 5% (w/v);
d) passing the ethanol carrier gas mixture resulting from gas stripping through an adsorber, ethanol from the gas mixture being adsorbed to an adsorber and the carrier gas being returned to the fermentation solution after leaving the adsorber.

The following process is also especially preferred in accordance with the invention:

A method for preparing ethanol, comprising
a) the fermentative reaction of C6 sugars to obtain ethanol in a fermentation solution containing C5 and C6 sugars in a first reactor;
b) the subsequent step-wise or continuous feeding of the fermentation solution containing ethanol and C5 sugar to a second reactor,
c) the fermentative reaction of the C5 sugar in the fermentation solution to form ethanol in the second reactor;
d) the in-situ removal of the ethanol from the second reactor by gas stripping with the aid of a carrier gas;
e) passing the ethanol carrier gas mixture obtained by gas stripping through an adsorber where ethanol is adsorbed from the gas mixture to an adsorber,
f) desorption of adsorbed ethanol, the carrier gas being returned to the fermentation solution of the second reactor after leaving the adsorber wherein feeding of the fermentation solution containing ethanol and C5 sugar into the second reactor is conducted in such a manner that the ethanol concentration in the fermentation solution in the second reactor is kept below 5% (w/v).

In this process, the ethanol concentration is preferably kept below 5% (w/v) by adjusting the feed rate of the fermentation solution containing ethanol and C5 sugar into the second fermenter and/or the gassing rate during gas stripping and/or the amount of adsorber are adjusted.

The adsorber preferably contains a zeolite. In a particularly preferred embodiment, the heat released during adsorption is used for desorption, It is further preferred to keep the ethanol concentration in the fermentation solution below 5% (w/v).

Fermentation, gas stripping, adsorption and desorption as well as the final purification are preferably linked to each other so that the energy costs for purifying the final product ethanol are significantly reduced vis-à-vis conventional processes.

EXAMPLES

The invention will be illustrated in further detail in the following examples which are not limiting.

Example 1

In-situ Separation of Ethanol During Fermentation

A) Fermentation with *Pachysolen tannophilus* in a Synthetic Medium

Figure 2:
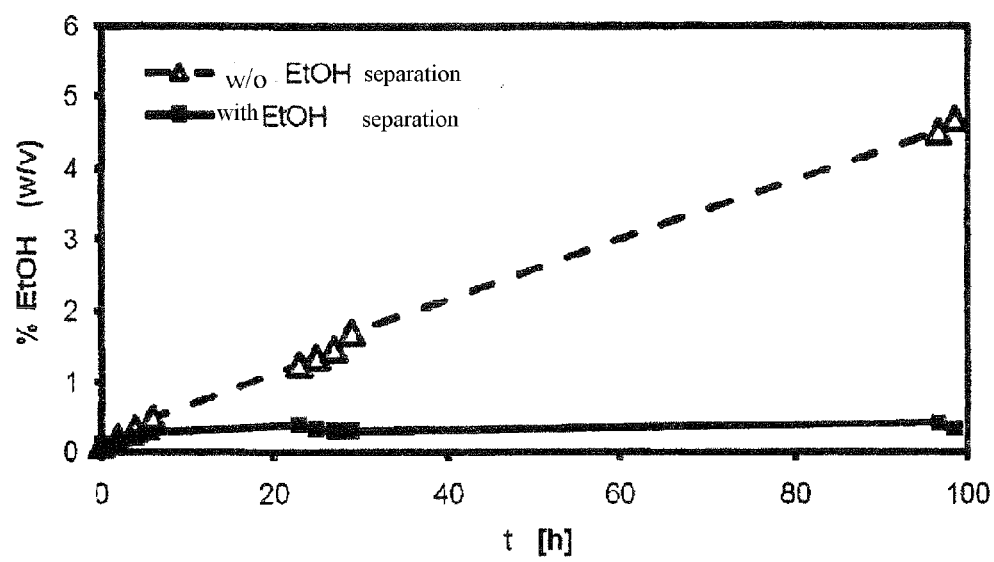
FIG. 2 shows the development of the ethanol concentration during fermentation according to example 1A.

*Pachysolen tannophilus* (DSMZ, Braunschweig) was fermented with and without in-situ separation of ethanol under otherwise identical conditions at 30° C. for 100 hours. The fermentation medium consisted of 5 g/L of Bacto™ Yeast Extract (Becton, Dickinson Co., France), 6.7 g/L of 1× Difco Yeast Nitrogen Base w/o Amino Acids (Becton, Dickinson Co., France), adding distilled $H_2O$ to a total amount of 350 mL. Two 350 mL cultures each were prepared in 1 L Schott glass bottles with gastight GL 45 multiple distributors on the bottle (Bola, Grünsfeld) which had three GL14 inlets for screw-on tubing. In each case, 35 g of glucose were used as the carbon source in the fed-batch mode. One inlet was used for taking samples. The carrier gas (nitrogen) was fed into the fermentation medium through another inlet via a PA 12–8×6×1 tubing (Riegler, Bad Urach) and a glass frit. Through the third inlet, the carrier gas was passed in a tubing from the bottle head to a 100 mL glass frit column filled with a zeolite (prepared according to the U.S. Pat. No. 7,244,409 B2) for in-situ separation. The glass frit column was not loaded for the reference experiment. The gas cycle was driven by a membrane pump (KNF, Freiburg) operated between the glass frit column and the Schott glass bottles at a rate of 1.5 l/min. 2.5% (w/v) each of glucose (Sigma-Aldrich, Munich) were added at 0, 24, 48 and 72 hours. The amount of ethanol in the fermentation medium was determined by gas chromatography (Trade GC, Thermo Fisher). The result of the experiment is shown in FIG. 2. The GC determinations of the ethanol concentrations in the media show that the ethanol concentration in the fermentation medium can be held below 1% (w/v) of ethanol as a result of the in-situ separation, thus avoiding inhibitions caused by the ethanol concentration.

Under otherwise identical conditions as described above, a mixture of C5 and C6 sugars and without in situ separation of ethanol was also fermented, using 2.45 g of glucose and 10.5 g of xylose as the carbon source in a batch mode.

B) Fermentation with *Pichia stipitis* on a Ligno-Cellulose Substrate

*Pichia stipitis* (DSMZ, Braunschweig, Germany) was fermented with and without in-situ separation of ethanol under otherwise identical conditions for 95 hours at 30° C. under micro-aerobic conditions. The fermentation medium was a pre-treated and hydrolysed ligno-cellulose substrate. Two cultures of 800 mL each were prepared in a small 1.4 l fermenter. Since a ligno-cellulose substrate was used, 56 g/L of glucose and 31 g/L of xylose were contained as the carbon source in each case. Fermentation was conducted in a batch mode. One of the two cultivations was performed without in-situ stripping, the other with in-situ stripping. In the latter case, the gas stream was adjusted to 2 vvm via a rotameter (Vöglin, Aesch, Switzerland). Using a membrane pump (KNF, Freiburg, Germany) and gastight tubing (VWR, Darmstadt, Germany), the gas stream was passed through a glass column and then returned. The glass column was packed with 535 g of zeolite granules (ZSM-5; $SiO_2/Al2O_3$=200, Süd-Chemie AG, Germany). Samples were taken during fermentation and the ethanol content quantified by gas chromatography (Trace GC, Thermo Fisher, Germany) and the sugars by HPLC (Dionex, U.S.A.). In addition, the weight increase of the zeolite and the ratio of water in the adsorbed mixture was determined by Karl Fischer titration (Schott Instruments, Germany). It was further assumed that only water and ethanol are adsorbed under the existing conditions. It was possible to confirm this assumption in preliminary experiments. This permits concluding the ethanol ratio from the water content.

Figure 3:
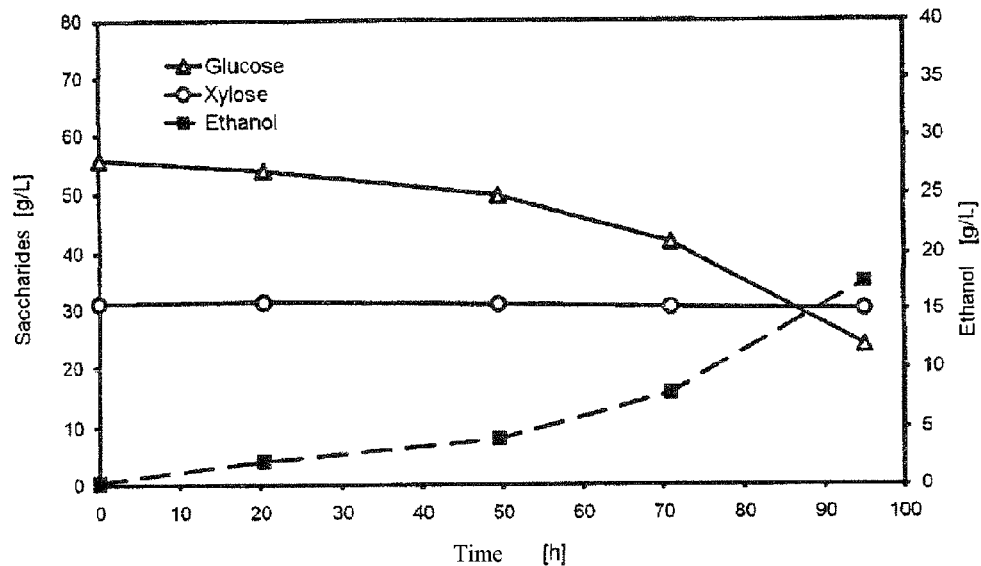
FIG. 3 shows the development of the glucose, xylose and ethanol concentration during fermentation according to example 1B.
Figure 3:
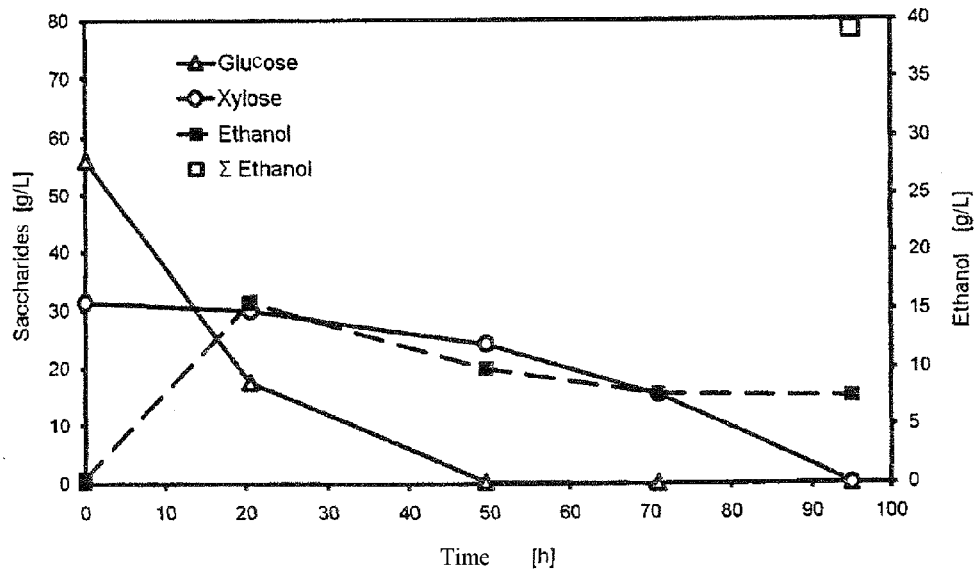

The results of the experiment are shown in FIG. 3 (top: without in-situ stripping; bottom: with in-situ stripping). The results of the analysis of the fermentation broths show that the ethanol concentration of the fermentation medium can be kept below 2% (w/v) of ethanol by the in-situ separation. This helps avoid inhibitions by the ethanol concentration and permits the fermentation of the xylose portion.

C) Sequential Fermentation with *Saccharomyces cerevisiae* and *Pachysolen tannophilus* on a Ligno-Cellulose Substrate Unless indicated otherwise, all of the conditions in this experiment were identical to example 1B. Sequential fermentation was performed, first conducting the fermentation of the glucose anaerobically in a batch mode with *Saccharomyces cerevisiae* (DSMZ, Braunschweig, Germany) without in-situ gas stripping. The solution used contained 63 g/L of glucose and 32 g/L of xylose. Fermentation was performed in the batch mode. The substrate thus obtained which contained xylose and ethanol was fermented with *Pachysolen tannophilus* (DSMZ, Braunschweig, Germany) under microaerobic conditions for 114 hours at 30° C. in the batch mode with in-situ separation of ethanol. The result of this second fermentation phase is shown in FIG. 4 (top). It is evident that the C5 fermentation does not start until the ethanol concentration has been reduced to values below about 15 g/L by gas stripping. In other words, only gas stripping makes fermentation of the C5 sugars possible.

In a second experiment with sequential fermentation, fermentation of the glucose was conducted with *Pachysolen tannophilis* (DSMZ, Braunschweig, Germany) in a batch mode. The substrate recovered which contained xylose and ethanol was fermented as a feed solution under microaerobic conditions with in-situ separation of ethanol in a batch mode with the same organism for 72 hours at 40° C. The starting volume for the fed-batch cultivation was 300 mL; these 300 mL were not pre-fermented. The results of the fed-batch phase are shown in FIG. 4 (bottom, between the two marking lines). It is evident that the combination of a fed-batch mode and gas stripping makes it possible to keep the ethanol concentration at a particularly low level during C5 fermentation.

Figure 5:
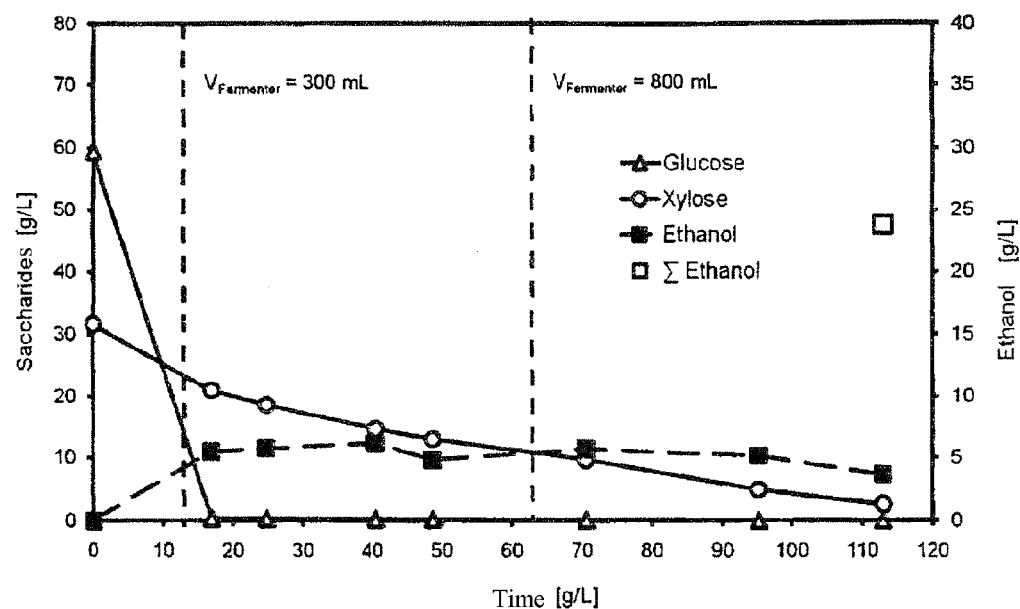
FIG. 5 shows the development of the glucose, xylose and ethanol concentration during fermentation according to example 1D.

D) Fed-batch Fermentation with *Pachysolen tannophilus* on a Ligno-Cellulose Substrate Unless indicated otherwise, all the conditions in this experiment were identical to example 1B. The sugars contained in the ligno-cellulose substrate, 60 g/L of glucose and 32 g/L of xylose, were fermented with *Pachysolen tannophilus* (DSMZ, Braunschweig, Germany) while both present in the starting volume and the feed solution in a fed-batch mode under micro-aerobic conditions a 40° C. for 113 hours. The starting volume was 300 mL. The result of the experiment is shown in FIG. 5. The results of the analysis of the fermentation broths show that the ethanol concentration in the fed-batch mode at 40° C. can be kept below 1.5% and the simultaneous reaction both of the C6 and the C5 sugars was made possible with the combination of a fed-batch mode and in situ gas stripping.

Example 2

Concentration of a 7.5% (w/v) Ethanol-water Solution by Gas Stripping, Adsorption, Desorption and Condensation 100 mL of a 7.5% (w/v) ethanol-water solution were stripped with a volume stream of 0.5 L/min of air for 24 hours, using a membrane pump (KNF Neuberger, Freiburg, Germany), a volume stream controller (Swagelok, Garching, Germany), and a gas scrubber bottle (WWR, Bruchsal, Germany). The gas stream was passed through a glass column (VWR, Bruchsal, Germany) packed with 91 g of the zeolite (prepared according to the U.S. Pat. No. 7,244,409 B2). Heating coils were arranged inside the column. Gas stripping and adsorption took place at room temperature. Then the temperature was raised to 150° C. in a linear manner within 90 minutes with the aid of the heating coils and via the column wall. The desorbed ethanol was condensed in a cold trap at 20° C. The absolute pressure was 800 mbar both for adsorption and desorption. The carrier gas stream was directed in a circuit.

Ethanol concentrations:
Starting solution: 7.48% (w/v)
Solution after gas stripping: 2.15% (w/v)
Condensate: 44.92% (w/v)

Example 3

Selective Adsorption to Activated Carbon and Zeolite

A) Gas Stripping, Adsorption and Desorption with a Zeolite and Comparison with Literature Data Gas stripping and adsorption were conducted in the same manner as described in example 2. However, the volume of the charge was increased to 1 L so that the change in concentration by ethanol adsorption was comparatively small and the concentration hence almost constant (steady state). The concentration of adsorbed ethanol was determined by gas chromatography (Trace GC, Thermo Fisher).

Figure 6:
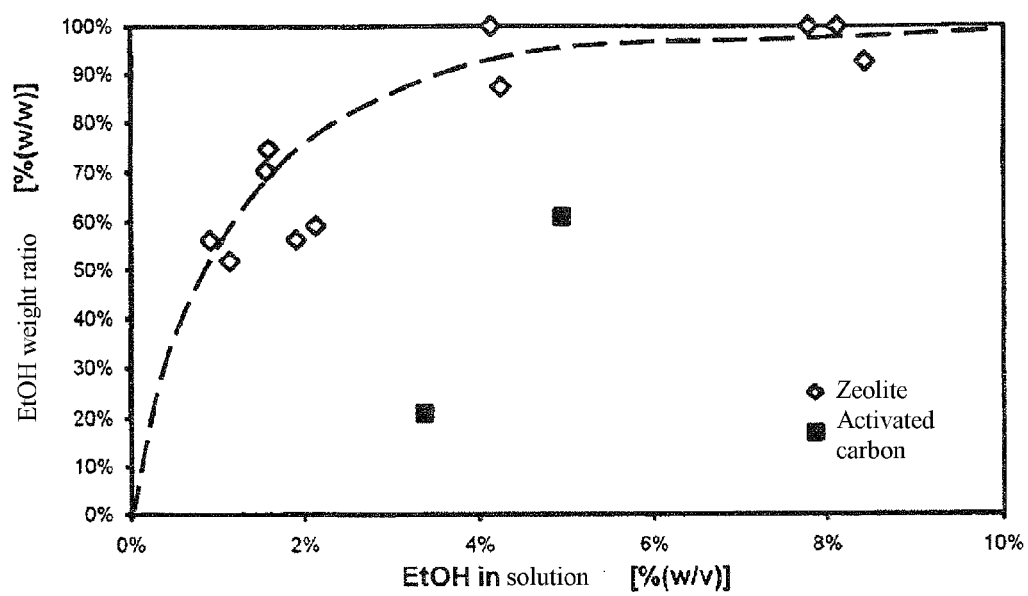
FIG. 6 shows a comparison between the zeolite used according to the invention and activated carbon with regard to ethanol selectivity.
Figure 7:
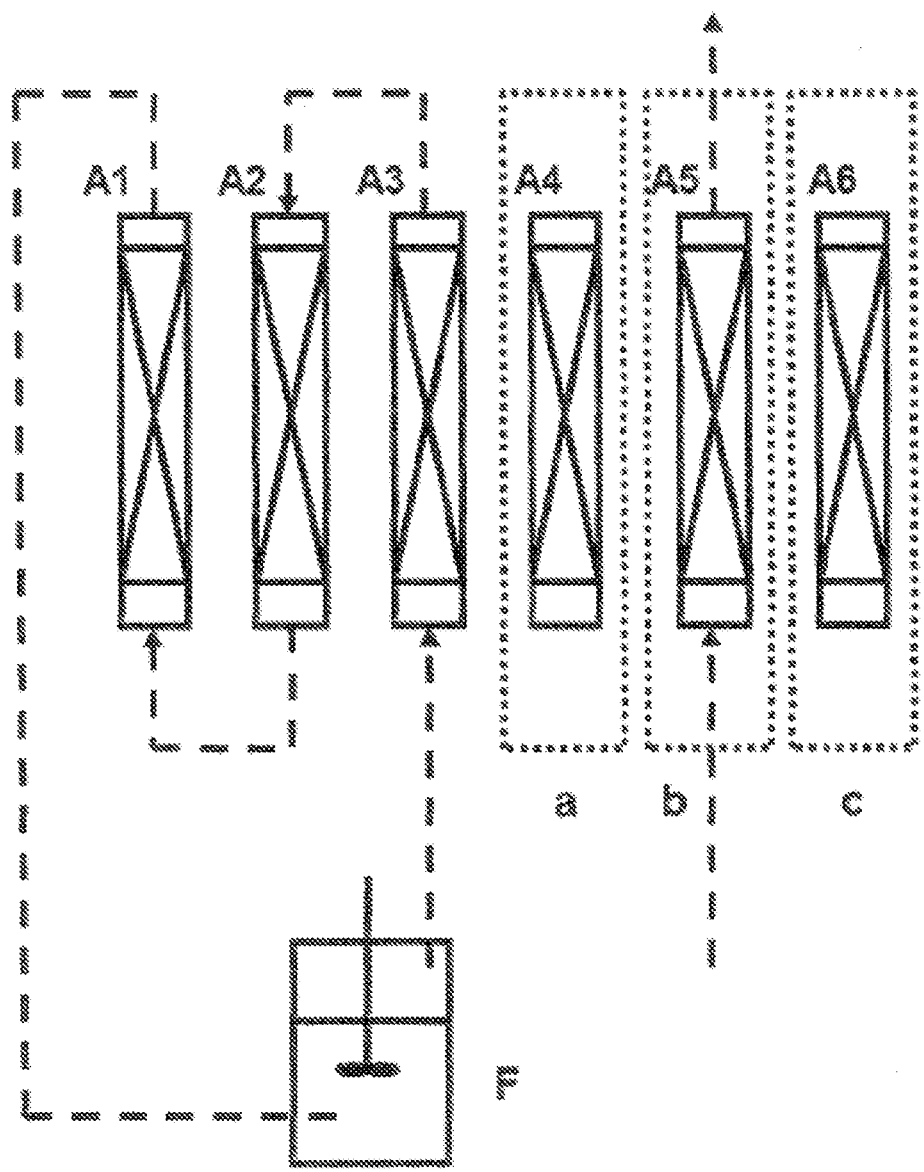
FIG. 7 shows an embodiment of the invention with a rotary configuration.

Walsh et al. list two experiments in Table IV where the ethanol concentration in the liquid was below 5% (w/v) (4.94% (w/v) and 3.37% (w/v)). A calculation of the ethanol weight ratios from the weights adsorbed results in 61% (w/w) and 21% (w/w) (see chart, red dots). This means that the ethanol weight ratios in the process of the invention using a zeolite were considerably higher (see FIG. 6).

B) Direct Comparison of Zeolite and Activated Carbon in Gas Stripping and Adsorption In two otherwise identical experiments, 90 g of zeolite on the one hand and 90 g of activated carbon on the other were packed into a glass column (VWR, Bruchsal, Germany). In each case, 250 mL of a 5% (w/v) ethanol water solution were stripped at 1 vvm for 24 hours. Otherwise the design was the same as in example 2, using a membrane pump (KNF Neuberger, Freiburg, Germany), a volume current controller (Swagelok, Garching, Germany) and a gas scrubber bottle (VWR, Bruchsal, Germany). After 24 hours, the experiment was terminated, the weight increase of the pack determined and the ethanol concentration quantified by gas chromatography (Trace GC, Thermo Fisher). Since the system is closed, the ethanol stripped from the solution must have been adsorbed on the zeolite or, respectively, the activated carbon. The remaining weight increase is due to water. The amounts of ethanol and water adsorbed are calculated by a mass balance and thus the following ethanol weight ratios in the adsorbed mixture determined:

Zeolite: 97.4% (w/v)
Activated carbon: 49.8% (w/v)

It has been shown, therefore, that the use of a zeolite has significant advantages vis-à-vis activated carbon as the adsorption to zeolites is clearly more selective. With a view to the cost of energy, this is a decisive advantage for the subsequent thermal purification.

The technical effect of the present application cannot be achieved with activated carbon, for activated carbon binds significantly more water than the zeolite. Thus the decisive advantage of zeolite vis-à-vis activated carbon is the higher selectivity, i.e. the zeolite preferably binds ethanol and just a little water. This simplifies the subsequent purification of the desorbed ethanol (less mass has to be desorbed, the rectification column is smaller and the cost of energy is drastically reduced).

The invention claimed is:

1. A method for preparing ethanol comprising:
    a) fermentatively reacting C5 and/or C6 sugars in a fermentation solution, to yield a fermentation solution comprising volatile components, said volatile components comprising ethanol;
    b) converting said ethanol to a gas phase, to yield gas phase ethanol, wherein said converting to said gas phase is done in-situ, said converting comprising stripping with a carrier gas, said carrier gas comprising carbon dioxide formed during fermentation of said C5 and/or C6 sugars;
    c) removing the gas phase ethanol, the removal comprising passing the gas phase ethanol through a zeolite adsorber, wherein the zeolite adsorber has a $SiO_2$/$Al_2O_3$ ratio from 200 to 1000; wherein gas phase ethanol is adsorbed to the zeolite adsorber to yield adsorbed ethanol;
    d) desorbing the adsorbed ethanol from the zeolite adsorber.

2. The method according to claim 1, wherein C5 sugars present in the fermentation solution are reacted to form ethanol.

3. The method according to claim 1, wherein the amount of the adsorbed ethanol at the end of fermentation is at least 20% of the maximum amount of ethanol adsorbed by the zeolite adsorber.

4. The method according to claim 1, wherein the adsorption takes place at a temperature that does not exceed the temperature of the ethanol-carrier gas mixture when leaving the fermentation solution.

5. The method according to claim 1, wherein the carrier gas is returned to the fermentation solution after leaving the zeolite adsorber.

6. The method according to claim 1, wherein gas stripping is carried out at a rate between 0.1 and 10 vvm.

7. The method according to claim 1, wherein the carrier gas is carbon dioxide formed during fermentation.

8. The method according to claim 1, wherein ethanol is adsorbed from the gas mixture to the zeolite adsorber at a temperature between 10 and 100 °C. and at a pressure between 0.5 and 10 bar.

9. The method according to claim 1, wherein the amount of the adsorbed ethanol at the end of fermentation is at least 50% of the maximum amount of ethanol adsorbed by the adsorber.

10. The method according to claim 1, wherein the amount of the adsorbed ethanol at the end of fermentation is at least 90% of the maximum amount of ethanol adsorbed by the adsorber.

11. The method according to claim 1, wherein gas stripping is carried out at a rate between 0.5 and 5 vvm.

12. The method according to claim 1, wherein ethanol is adsorbed from the gas mixture to the zeolite adsorber at a temperature between 20 and 50° C. and at a pressure between 1 and 2 bar.

13. The method according to claim 1, wherein gas stripping is carried out in a gas stripping column connected to the fermenter which is continuously fed with the fermentation solution and the efflux of which is returned to the fermenter.

14. The method according to claim 13, wherein the gas stripping column is operated in a counter-flow and/or contains filler materials.

15. The method according to claim 13, wherein a charge and discharge of thermal energy in the gas stripping column takes place through heating coils in addition to the wall of the column and the carrier gas stream.

16. The method according to claim 13, wherein the gas stripping column comprises several adsorption/desorption columns operated in parallel and/or in series.

17. The method according to claim 16, wherein the columns are filled with different kinds of adsorbents.

18. The method according to claim 16, wherein the columns are operated in parallel and/or in series and adsorption in one column is carried out simultaneously with desorption in another column.

* * * * *